United States Patent
Kühn et al.

(10) Patent No.: US 11,077,021 B2
(45) Date of Patent: Aug. 3, 2021

(54) TWO-CHAMBER CARPULE

(71) Applicant: Sanofi-Aventis Deutschland GMBH, Frankfurt am Main (DE)

(72) Inventors: Bernd Kühn, Frankfurt am Main (DE); Jörn Möckel, Frankfurt am Main (DE); Werner Seiferlein, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 398 days.

(21) Appl. No.: 16/076,242

(22) PCT Filed: Feb. 9, 2017

(86) PCT No.: PCT/EP2017/052808
§ 371 (c)(1),
(2) Date: Aug. 7, 2018

(87) PCT Pub. No.: WO2017/137470
PCT Pub. Date: Aug. 17, 2017

(65) Prior Publication Data
US 2019/0262233 A1 Aug. 29, 2019

(30) Foreign Application Priority Data
Feb. 9, 2016 (EP) .................................. 16154816

(51) Int. Cl.
*A61J 1/06* (2006.01)
*A61M 5/28* (2006.01)
(Continued)

(52) U.S. Cl.
CPC ............. *A61J 1/2093* (2013.01); *A61J 1/062* (2013.01); *A61J 1/065* (2013.01); *A61J 1/2041* (2015.05);
(Continued)

(58) Field of Classification Search
CPC ........ A61J 1/2093; A61J 1/062; A61J 1/2041; A61J 1/065; A61J 1/00; A61J 1/06;
(Continued)

(56) References Cited

U.S. PATENT DOCUMENTS 3,016,896 A 1/1962 Sickle
3,279,654 A * 10/1966 Pierick .............. A61M 5/31596
222/137
(Continued)

FOREIGN PATENT DOCUMENTS

CN 1185024 1/2005
CN 105188636 12/2015
(Continued)

OTHER PUBLICATIONS

International Search Report and Written Opinion in Application No. PCT/EP2017/052808, dated Apr. 20, 2017, 11 pages.
(Continued)

*Primary Examiner* — Catharine L Anderson
(74) *Attorney, Agent, or Firm* — Fish & Richardson P.C.

(57) ABSTRACT

The disclosure provides a two-chamber carpule comprising two-chambers adapted to be joined together. Each chamber is adapted to contain a medicament component. The carpule further comprises a bevel arranged on a circumference of at least one of the chambers in a transition area. The bevel extends from one chamber to the other chamber.

20 Claims, 18 Drawing Sheets

(51) Int. Cl.
*A61J 1/20* (2006.01)
*B65B 3/00* (2006.01)
*B65B 29/10* (2006.01)
*A61M 5/20* (2006.01)
*A61M 5/31* (2006.01)
*A61M 5/24* (2006.01)

(52) U.S. Cl.
CPC ........ *A61M 5/2066* (2013.01); *A61M 5/2448* (2013.01); *A61M 5/284* (2013.01); *A61M 5/3129* (2013.01); *B65B 3/003* (2013.01); *B65B 29/10* (2013.01)

(58) Field of Classification Search
CPC ............ A61J 1/20; A61J 1/2003; A61J 1/202; A61M 5/2066; A61M 5/2448; A61M 5/284; A61M 5/3129; A61M 5/2006; A61M 5/285; A61M 2005/2451; A61M 2005/287; B65B 3/003; B65B 29/10
See application file for complete search history.

(56) References Cited

U.S. PATENT DOCUMENTS

| | | | | |
|---|---|---|---|---|
| 3,351,058 A | * | 11/1967 | Webb | ................... A61M 5/284 |
| | | | | 604/87 |
| 3,756,390 A | * | 9/1973 | Abbey | .................. A61M 5/284 |
| | | | | 206/219 |
| 3,881,484 A | * | 5/1975 | Gidcumb, Jr. | .... A61M 5/31596 |
| | | | | 604/89 |
| 4,235,235 A | | 11/1980 | Bekkering | |
| 4,254,768 A | * | 3/1981 | Ty | ......................... A61M 5/284 |
| | | | | 604/518 |
| 4,743,229 A | * | 5/1988 | Chu | ..................... A61J 1/2096 |
| | | | | 604/82 |
| 8,376,987 B2 | | 2/2013 | Kuhn | |
| 2004/0249339 A1 | | 12/2004 | Willis et al. | |
| 2011/0060274 A1 | | 3/2011 | Kuhn | |
| 2012/0118139 A1 | | 5/2012 | Seiferlein et al. | |
| 2013/0165853 A1 | | 6/2013 | Kawamura | |

FOREIGN PATENT DOCUMENTS

| | | |
|---|---|---|
| JP | 2001-212236 | 8/2001 |
| JP | 2003-534062 | 11/2003 |
| JP | 2010-528792 | 8/2010 |
| JP | 2013-132349 | 7/2013 |
| WO | WO 01/89614 | 11/2001 |
| WO | WO 2009/077091 | 6/2009 |
| WO | WO 2014/140152 | 9/2014 |

OTHER PUBLICATIONS

International Preliminary Report on Patentability in Application No. PCT/EP2017/052808, dated Aug. 14, 2018, 8 pages.

* cited by examiner

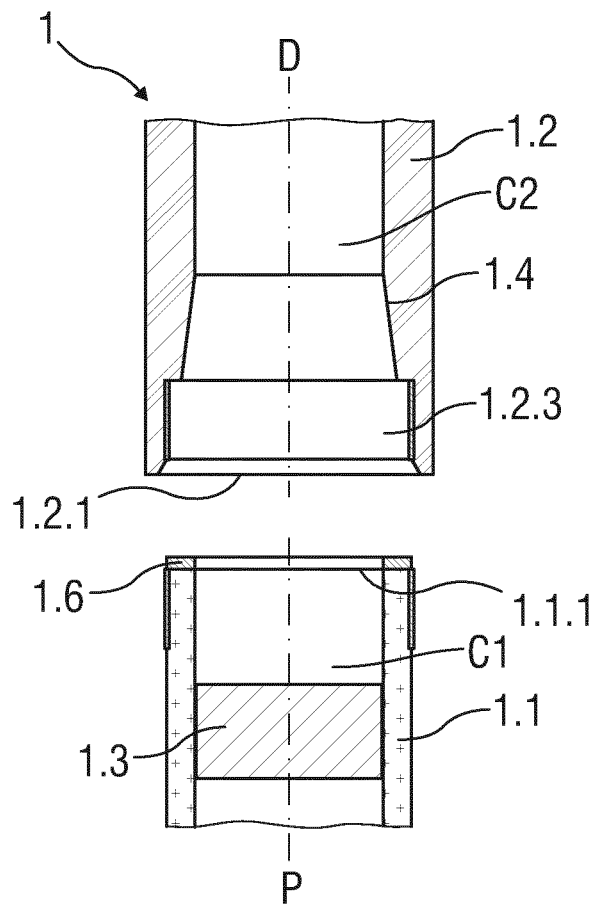
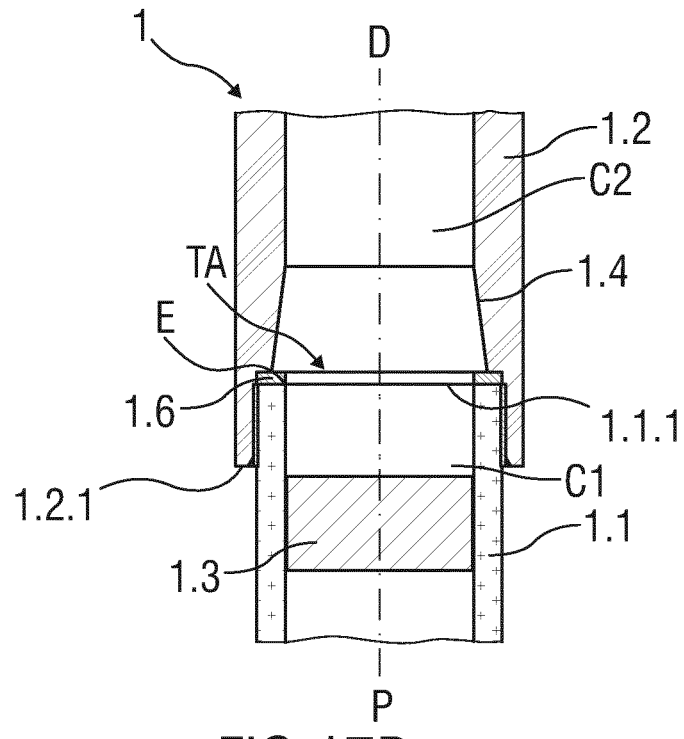
FIG 17A
FIG 17B

TWO-CHAMBER CARPULE

CROSS REFERENCE TO RELATED APPLICATIONS

The present application is the national stage entry of International Patent Application No. PCT/EP2017/052808, filed on Feb. 9, 2017, and claims priority to Application No. EP 16154816.9, filed on Feb. 9, 2016, the disclosures of which are incorporated herein by reference.

TECHNICAL FIELD

The disclosure generally relates to a two-chamber carpule and to a method of assembly of such a two-chamber carpule.

BACKGROUND

Two-chamber carpules are well known as packaging systems for medicaments that require separation of two components, e.g. a dry powder and a liquid carrier or two liquid components, during storage. Shortly before administration the liquid carrier is transferred from its chamber via a bypass to the chamber storing the dry powder in order to be mixed and as a result forming the final medicament to be administered to the patient For example, WO 2009/077091 A1 and U.S. Pat. No. 8,376,987 B2 disclose a two-chamber device.

Two-chamber carpules containing liquid carrier and dry powder formulation integrated in the same container system as a final medicament cannot be sterilized by moist heat sterilization processes and have to be manufactured applying aseptic technologies to ensure sterility. Moist heat sterilization is the preferred and recommended sterilization process leading to the highest level of sterility assurance and should be applied at least for liquid aqueous components.

SUMMARY

A two-chamber carpule comprises two-chambers adapted to be joined together, wherein each chamber contains a part of the medicament composition. The two-chamber carpule further comprises a bevel arranged on a circumference of at least one of the chambers in a transition area from one chamber to the other chamber. In particular, the bevel is arranged on a circumference of a distal chamber in a transition area from a proximal chamber to the distal chamber. Here, the transition area is a passage in the two-chamber carpule through which a plug moves during axial transition from the proximal chamber to the distal chamber.

As the proximal chamber typically contains a liquid carrier that is used as a carrier for reconstitution products and could undergo terminal moist heat sterilization, it is desirable to separately sterilize this component of the product by moist heat sterilization, whereas remaining process steps may rely on aseptic manufacturing processes. To enable separate moist heat sterilization for the liquid component, the present two-chamber carpule is configured with two separate chambers, one for the liquid and one for the dry powder component or for a further liquid formulation.

In an exemplary embodiment, each chamber is formed by a separate component and the separate components are axially joined together, wherein the bevel is arranged on an inner circumference of at least one of the components in the transition area from one component to the other component, wherein the transition area provides an edge in order to block a movement of a plug in a determined direction. In particular, the bevel is arranged on an inner circumference of a distal component in a transition area from a proximal component to the distal component. Here, the transition area is a passage in the two-chamber carpule through which a plug moves during axial transition from the proximal component to the distal component.

The two-chamber carpule thus enables un-hindered movement of the plug from the proximal component to the distal component and a tight connection between the components; thereby fulfilling quality attributes regarding requirements for industrial automated processes, tight connection and full technical functionality. That means in detail, the two-chamber carpule allows high-speed automated industrial manufacturing and assembly process, in particular in line with current Good Manufacturing Practice (GMP) in order to avoid the generation of particles during the manufacturing and assembling process in a sterile pharmaceutical manufacturing area. The tight connections are required to ensure microbiological quality of the assembled two-chamber carpule, i.e. sterility during production, application and storage. Finally, the technical functionality of the two-chamber carpule is assured by avoiding producing edges that could impair the movement of the plug in a predefined direction, wherein the plug is disposed within at least one of the chambers. In particular, the bevel and the edge provide blocking an unintended movement of the plug in a proximal direction. This enables a reliable mixing of the medicament components, ensuring the ejection of a full medicament dose as well as avoiding contamination of the medicament components.

In an exemplary embodiment, the edge is formed by a distal end of one of the components that comprises an inner diameter less than an inner diameter of the other component in the transition area due to the bevel.

In an exemplary embodiment, at least one section of an inner circumference of the distal component is beveled such that an inner diameter of the distal component decreases in a direction away from the proximal component. Alternatively, at least one section of an inner circumference of the proximal component is beveled such that the inner diameter of the proximal component decreases in a direction facing the distal component. Furthermore, an inner diameter of the proximal component may be less than or equal to the inner diameter of the distal component having the bevel. This leads to a transition area having no ribs or angles for tilting a movement of the plug in a predefined direction, i.e. a distal direction for ejecting a medicament.

In an exemplary embodiment, one of the components is made from a plastic material and the other component is made from a glass material. For example, the proximal component made from glass material contains the liquid carrier and the distal component contains the dry powder. This enables moist heat sterilization for the liquid carrier separately from the dry powder as mentioned above. Alternatively, both components are made from glass material or from plastic material. Using the same material for both components enables a higher variation of connection types between the components.

An axial joint of the components may be realized by different connecting variants. For example, the components are firmly bonded together by an adhesive, a molded component, a fusion bond or by welding.

Alternatively, the components are joined together by at least one adapter enabling a snap fit, a screw thread or a combination of both connecting principles.

Further connecting types without the arrangement of an adapter would be a screw thread, a bayonet fitting, a snap fitting or a plug connection. The bayonet fitting may comprise at least one protrusion and a corresponding slot respectively arranged on an attachment attached to the components. The snap fitting may comprise at least one locking arm and a corresponding locking projection. The snap fitting may be improved by providing rough surfaces in an interface area of the components. Furthermore, the plug connection may be improved by an arrangement of a clamp element, i.e. a clamp ring.

In an exemplary embodiment, the two-chamber-carpule further comprises a sealing element that is arranged between the components and that will ensure tight connection between the components. In particular, the sealing element may be arranged in an interface area between an outer circumference of one of the components and an inner circumference of the other component.

In a further exemplary embodiment, a method of assembly of a two-chamber carpule is provided, comprising the following steps:
manufacturing the components,
filling the component with a medicament component and closing the component,
axially joining the components by a force fitting, form fitting or in a firmly bonding manner or in any combination thereof and
filling the other component with further medicament component and closing the other component.

The method allows reaching a high-speed assembly due to a linear movement of the connecting parts. Optionally, the component may be terminal sterilized and fed in to aseptic assembly zone.

In an exemplary embodiment, the component is closed at one side by inserting at least one plug into the chamber before the component is axially joined to the other component.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein:

FIG. 17A is a schematic longitudinal section of an exemplary embodiment of an inventive two-chamber carpule comprising two components made from different materials and a sealing element before assembly, FIG. 17B is a schematic longitudinal section of the inventive two-chamber carpule according to FIG. 17A in an assembled state.

Corresponding parts are marked with the same reference symbols in all figures.

DETAILED DESCRIPTION

Figure 1:
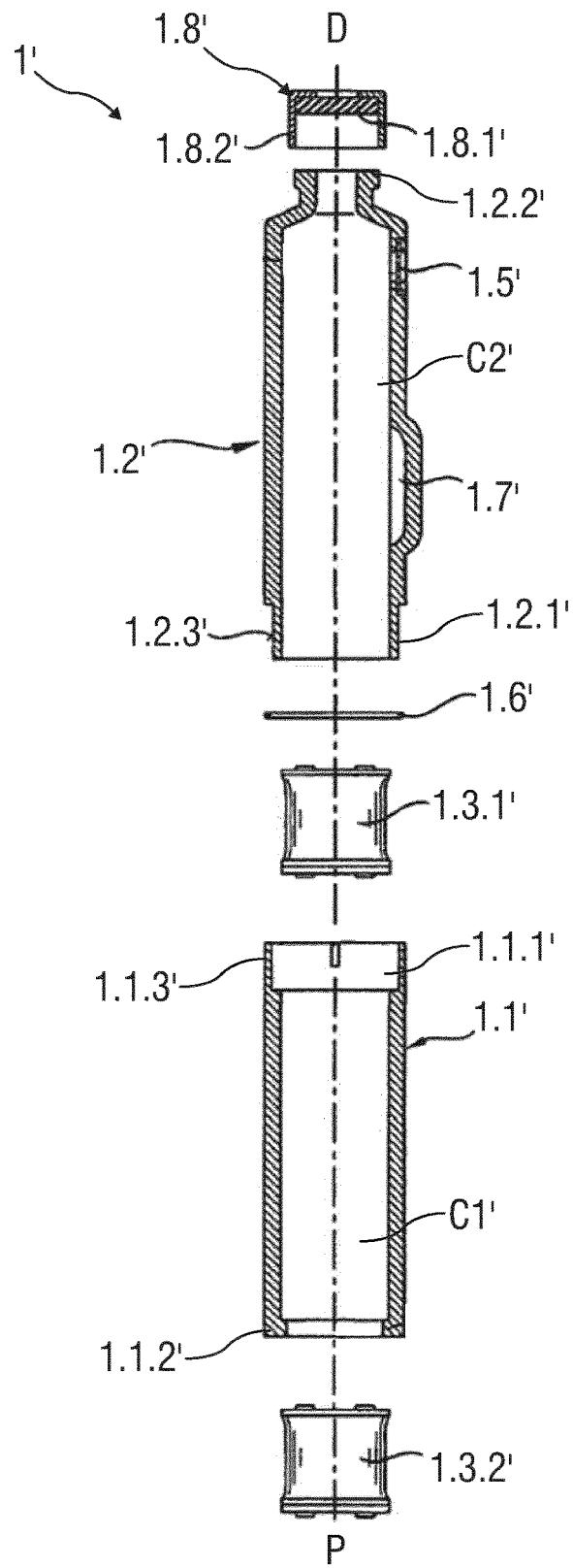
FIG. 1 is an exploded view of a schematic longitudinal section of a conventional two-chamber carpule comprising two components made from plastic materials before assembly.

FIG. 1 is an exploded view of a schematic longitudinal section of a conventional two-chamber carpule 1'. The illustrated two-chamber carpule 1' is known from WO 2009/077091 A1 referred to above.

The conventional two-chamber carpule 1' comprises two components 1.1', 1.2' respectively forming a chamber C1', C2' that contain a medicament component. The chambers 1.1', 1.2' may be made from a glass material, i.e. borosilicate glass or made from a plastic material, i.e. cycloolefin polymer or copolymer. Alternatively, one of the components 1.1', 1.2' is made from a glass material and another one of the components 1.1', 1.2' is made from a plastic material. A combination of the medicament components to be mixed to a final medicament for administration to a patient could be solid/liquid or liquid/liquid. Thus, the component 1.2' may contain a dry powder formulation or a liquid component and the other component 1.1' may comprise a liquid carrier.

Furthermore, the two-chamber carpule 1' comprises two plugs 1.3.1', 1.3.2' arranged within the components 1.1', 1.2 adapted to hermetically seal the components 1.1', 1.2'. The plugs 1.3.1', 1.3.2' may be respectively configured as a rubber bung made from an elastic material and dimensioned in a manner abutting an inner circumference of the components 1.1', 1.2', thereby being in a compressed state. According to the illustrated embodiment, one plug 1.3.2' is arranged within a proximal component 1.1' and the other plug 1.3.1' is arranged in an interface area of the components 1.1', 1.2'.

According to the present embodiment, the components 1.1', 1.2' are plugged together in the interface area, being additionally sealed by a sealing element 1.6'. A fluid-tight, gas permeable membrane 1.5' is arranged within a wall of a distal component 1.2' proximal behind a shoulder near a distal end 1.2.2' of the distal component 1.2'.

For mixing the medicament components, the plug 1.3'.1' has to be moved from the interface area in a distal direction D until passing a bypass 1.7' which is configured as an increased diameter of the distal component 1.2' comprising an axial length larger than an axial length of the plug 1.3.1' through which the liquid carrier may flow.

Furthermore, the proximal component 1.1' comprises an extension 1.1.3' on a distal end 1.1.1' facing the distal component 1.2' which extends an inner diameter of the lower component 1.1'.

The distal component 1.1 comprises a corresponding indentation 1.2.3', which reduces an outer diameter of the distal component 1.2' on a proximal end 1.2.1' facing the proximal component 1.1'.

Following, an exemplary assembly and filling of the conventional two-chamber carpule 1' will be described.

The plug 1.3.2' is inserted into the proximal component 1.1' and arranged on the proximal end 1.1.2' of the proximal component 1.2'. After that, the proximal component 1.2' is filled with a liquid component. Following this, the other plug 1.3.1' is inserted through a distal aperture of the proximal component 1.1' closing the proximal component 1.1' on its distal end 1.1.1'. The distal component 1.2' is then assembled onto the proximal component 1.1' creating a form fitting connection. The sealing element 1.6' is engaged in the interface area between the components 1.1', 1.2'. In particular, the sealing element 1.6' will be fixed to the extension 1.1.3' or to the indentation 1.2.3' before assembly. Alternatively, the sealing element 1.6' is inserted loosely between the components 1.1', 1.2' during assembly. For filling the distal component 1.2', the two-chamber carpule 1' is rotated about an angle of 180 degree and the distal component 1.2' is filled with a solid or liquid component, which is inserted into the distal component 1.2' through an open distal end 1.2.2'. Finally, the distal end 1.2.2' is closed by a cap 1.8' comprising a sealing disc 1.8.1' and a fixing sleeve 1.8.2'.

A connection between glass materials and between a plastic material and a glass material requires fulfilling quality attributes regarding industrial automated processes, tight connections and full technical functionality. That means in detail, the assembly of a component comprising such materials preferably allows high-speed automated industrial manufacturing and assembly process, in particular in line with current Good Manufacturing Practice (GMP) in order to avoid the generation of particles during the manufacturing and assembling process in a sterile pharmaceutical manufacturing area. The tight connections are required to ensure microbiological quality of the assembled component, i.e. sterility during production, storage and application/use.

Finally, a technical functionality of an inventive two-chamber carpule 1 should be assured by avoiding producing edges that could impair the movement of a plug 1.3 from a glass component to a plastic component (or from the plastic component to the glass component depending on the arrangement of the plug 1.3). Prior art does not provide solutions to fulfil these requirements.

Because prior art does not provide solutions to fulfil these requirements, the present disclosure provides an improved two-chamber carpule 1 as illustrated in the FIGS. 2A to 19 which fulfils all the mentioned quality attributes.

Figure 2A:
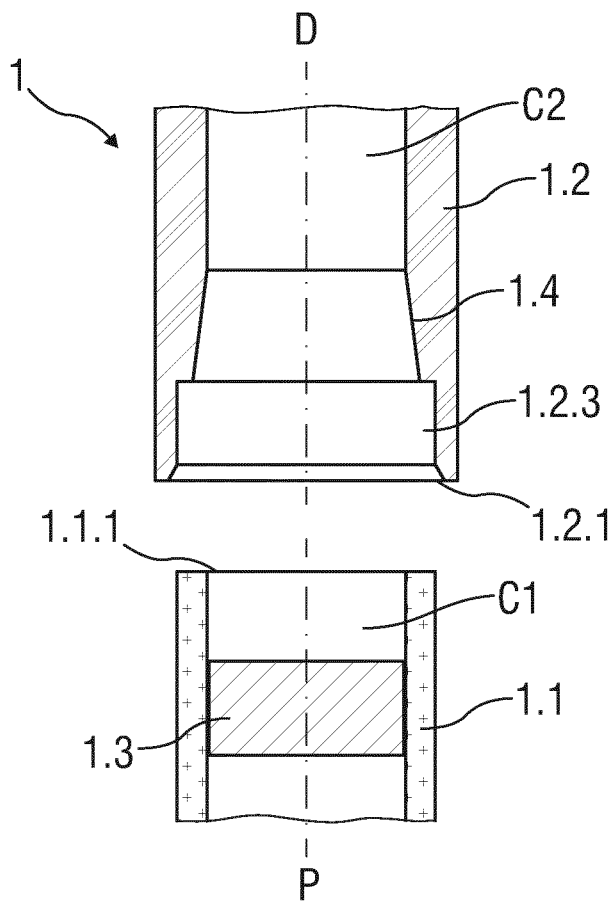
FIG. 2A is a schematic longitudinal section of a two-chamber carpule comprising two components made from different materials before assembly, wherein the two-chamber carpule represents a general embodiment of the present disclosure.
Figure 2B:
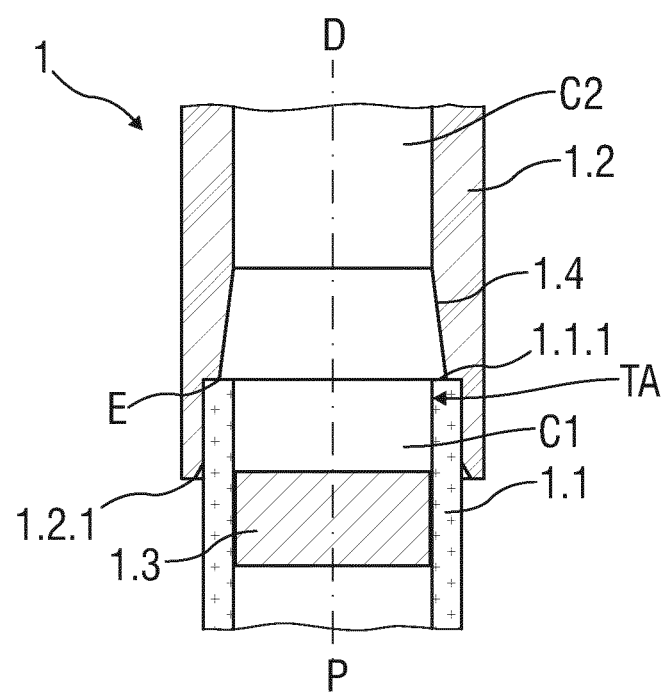
FIG. 2B is a schematic longitudinal section of the inventive two-chamber carpule according to FIG. 2A in an assembled state.

FIGS. 2A and 2B respectively show a schematic longitudinal section of an interface area of an exemplary embodiment of a two-chamber carpule 1, wherein FIG. 2A illustrates the inventive two-chamber carpule 1 before assembly and FIG. 2B illustrates the inventive two-chamber carpule 1 in an assembled state. Moreover, the present embodiment represents a general embodiment of the present disclosure.

In principle, the inventive two-chamber carpule 1 is very similar to the conventional two-chamber carpule 1'. The two-chamber carpule 1 comprises a proximal component 1.1 forming a chamber C1 and a distal component 1.2 forming another chamber C2, whereby the proximal component 1.1 may be made from a glass material and the distal component 1.2' may be made from a plastic material. The components 1.1, 1.2 may be configured as cylindrical elements.

In contrast to the conventional two-chamber carpule 1', the improved two-chamber carpule 1 comprises a bevel 1.4 arranged on an inner circumference of the distal component 1.2 in a manner that the inner diameter of the distal component 1.2 decreases in the distal direction D. The bevel 1.4 is dimensioned such that the inner diameter of the distal component 1.2 decreases until reaching the dimensions of the inner diameter of the proximal component 1.1. Thus, the inner diameter of the distal component 1.2 tapers in a truncated cone-shaped manner in the distal direction D away from the proximal component 1.1. A gradient of the bevel 1.4 may be different from the illustrated embodiment; in particular, it could be steeper or lower. The bevel 1.4 and the distal end 1.1.1 of the proximal component 1.1 form an edge E that is provided for blocking an unintended movement of a plug 1.3 in a proximal direction P. This enables a reliable mixing of the medicament components, ensuring the ejection of a full medicament dose as well as avoiding contamination of the medicament components.

Furthermore, the inner diameter of a proximal end 1.1.1 of the distal component 1.2 is larger than the inner diameter of the proximal component 1.1. In particular, the distal component 1.2 comprises a dent 1.2.3 in the inner circumference in order to receive the distal end 1.1.1 of the proximal component 1.1 at least in a form fitting manner, in particular in a form fitting and friction fitting manner. For this, a diameter of the dent 1.2.3 is slightly larger than an outer diameter of the proximal component 1.1. Connecting surfaces of the components 1.1, 1.2 after assembly are followed defined as an interface area.

As can be seen in FIG. 2B showing the assembled state of the two-chamber carpule 1, the inner diameter of the distal component 1.2 is larger than the inner diameter of the proximal component 1.1 in a transition area TA. If the plug 1.3 is now moved from the proximal component 1.1 into the distal component 1.2, the plug 1.3 can be release in the larger inner diameter of the distal component 1.2 without tilting in the transition area TA. Further movement of the plug 1.3 in the distal component 1.2 away from the proximal component 1.1 leads to a compression of the plug 1.3, and thus to a sealing of the interior space of the distal component 1.2. A return of the plug 1.3 in the proximal direction P of the proximal component 1.1 may be limited.

Figure 3:
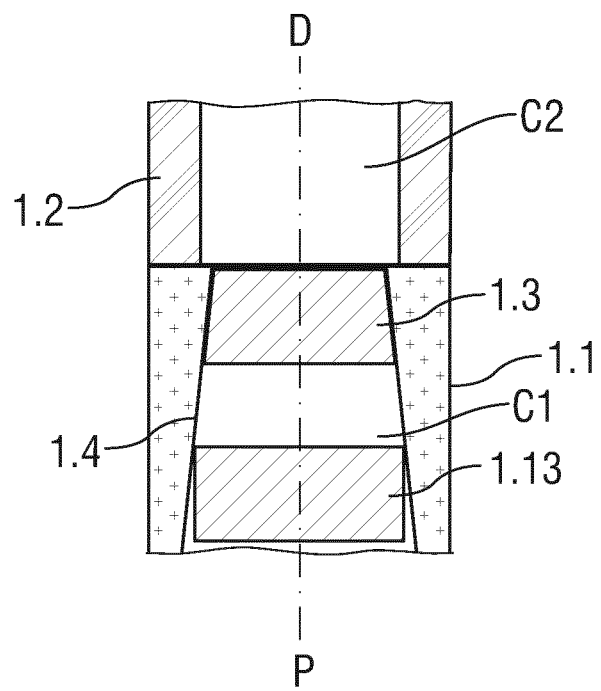
FIG. 3 is a schematic longitudinal section of an exemplary embodiment of an inventive two-chamber carpule comprising two components made from different materials and two plugs in an assembled state.
Figure 4:
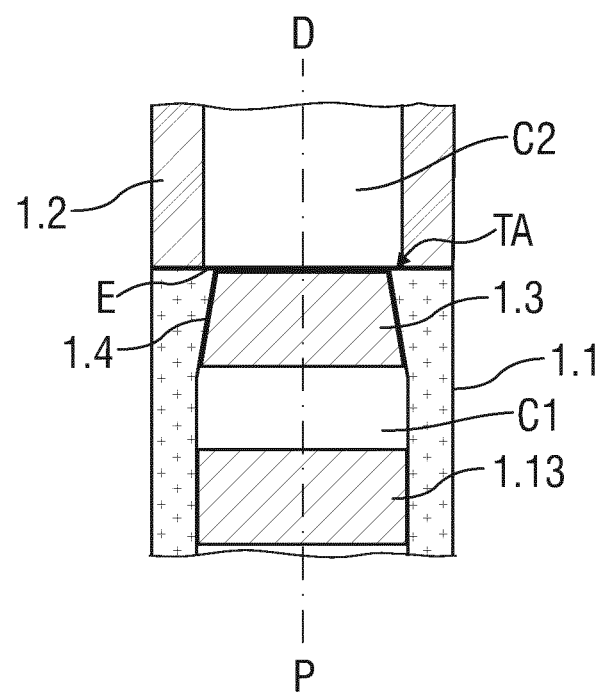
FIG. 4 is a schematic longitudinal section of a further exemplary embodiment of an inventive two-chamber carpule comprising two components made from different materials and two plugs in an assembled state.

FIGS. 3 and 4 respectively show a schematic longitudinal section of an exemplary embodiment of a two-chamber carpule 1 in an assembled state comprising two components 1.1, 1.2 and two plugs 1.3, 1.13.

In contrast to the exemplary embodiment described above, the bevel 1.4 is arranged on an inner circumference of the proximal component 1.1. According to the embodiment illustrated in FIG. 3, the bevel 1.4 is configured as a tapered inner diameter of the proximal component 1.1 decreasing continuously in the distal direction D along the entire length of the proximal component 1.1, i.e. as a draft angle.

According to the embodiment illustrated in FIG. 4, the bevel 1.4 is configured as a distal tapered section of the inner diameter of the proximal component 1.1. The rapid increased diameter of the inventive two-chamber carpule 1 is located in the transition area TA from the proximal component 1.1 to the distal component 1.2.

The tapered inner diameter of the proximal component 1.1 initially increases forces required for movement of the plug in the distal direction D. After passing the transition area TA, the forces are decreased down to a lower level. In case of using the inventive two-chamber carpule 1 in auto-injectors, a required force profile of spring elements can be adapted in compliance with the present embodiment since the available force potential in the proximal component 1.1 is greater than that in the distal component 1.2.

Following, different variants for connecting the components 1.1, 1.2 to each other will be described based on the general embodiment described in FIGS. 2A and 2B.

Figure 5A:
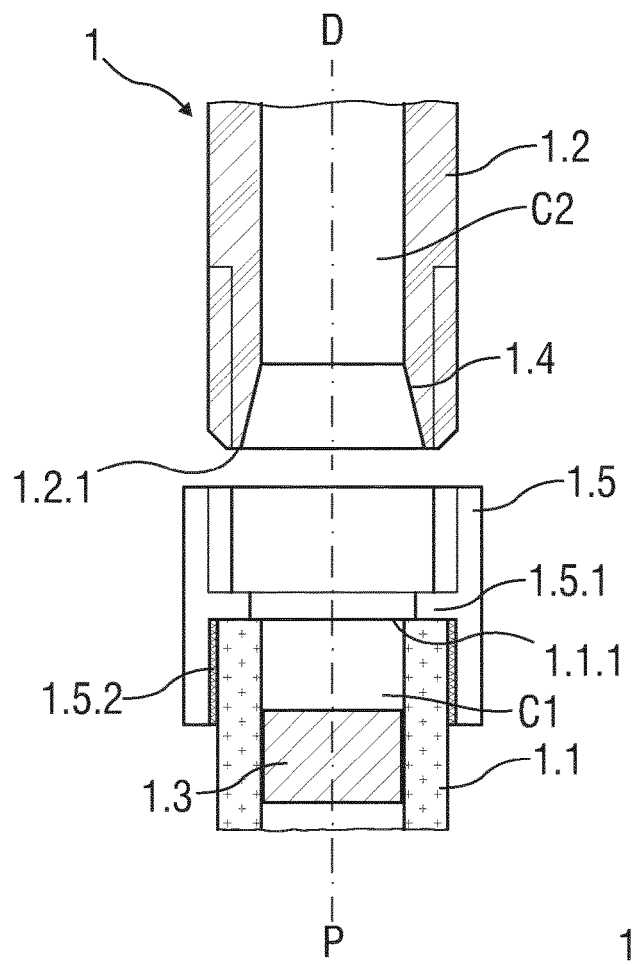
FIG. 5A is a schematic longitudinal section of an exemplary embodiment of an inventive two-chamber carpule comprising two components made from different materials and an adapter before assembly.
Figure 5B:
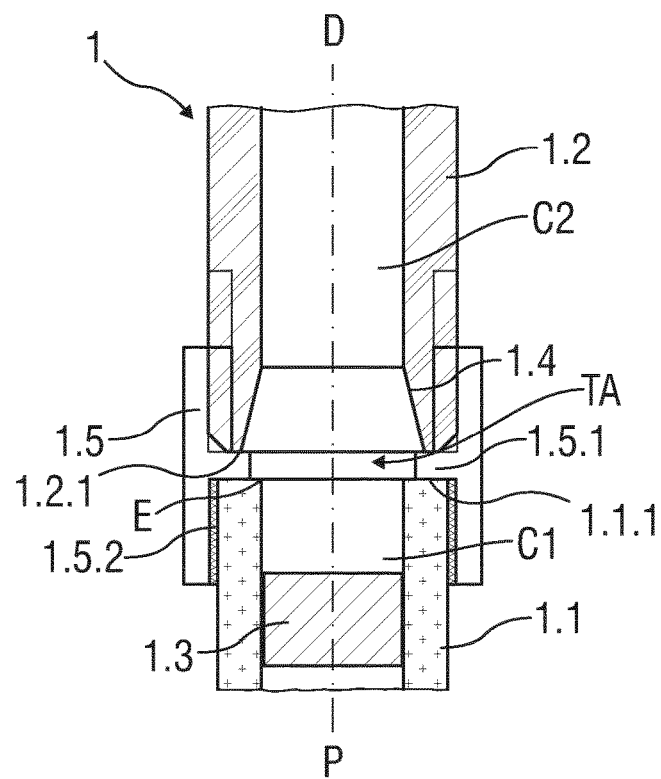
FIG. 5B is a schematic longitudinal section of the inventive two-chamber carpule according to FIG. 5A in an assembled state.
Figure 6:
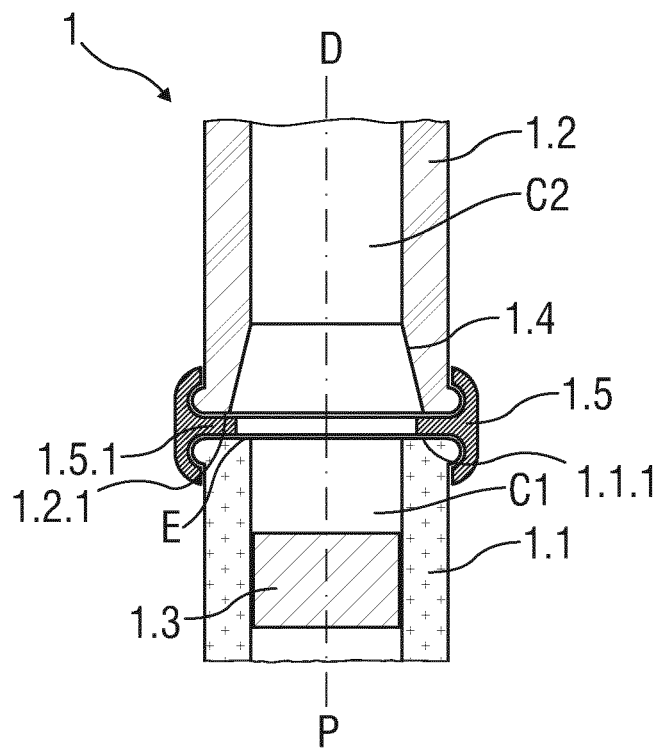
FIGS. 6, 7 are schematic longitudinal sections of exemplary embodiments of inventive two-chamber carpules respectively comprising two components made from different materials and further adapters in an assembled state.
Figure 7:
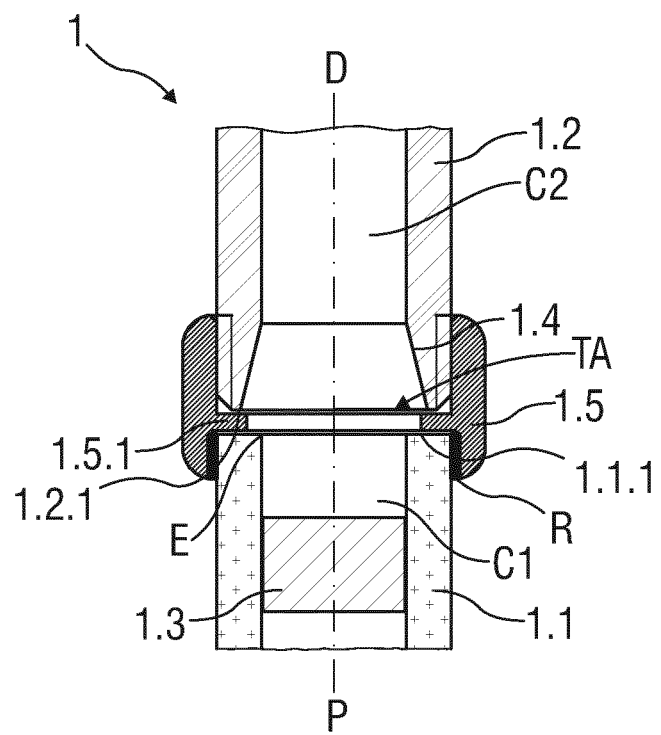

FIGS. 5A to 7 respectively show exemplary embodiments of a two-chamber carpule 1 joined together via an adapter 1.5. Here, FIG. 5A illustrates the two-chamber carpule 1 before assembly and FIGS. 5B, 6 and 7 illustrates the two-chamber carpule 1 in an assembled state.

The two-chamber carpule 1 is configured almost equally to the embodiment illustrated in FIGS. 2A and 2B. In addition to, the two-chamber carpule 1 comprises an adapter 1.5 by which the component 1.1, 1.2 may be joined together in a form fitting and force fitting manner.

According to the FIGS. 5A and 5B, the adapter 1.5 is fixed on the proximal component 1.1, thereby surrounding and projecting axially over the distal end 1.1.1 of the proximal component 1.1. The adapter 1.5 is configured as a hollow cylinder comprising a circumferential stop 1.5.1 projecting radially inside from an inner circumference of the adapter 1.5 and abutting the distal end 1.1.1 of the proximal component 1.1. Furthermore, the adapter 1.5 may be made from a plastic material, i.e. from polyolefin (PP, PE), cycloolefin (COC, COP), polyester, polyacrylate, acrylonitrile butadiene styrene, polyoxymethylene or other pharmaceutically acceptable plastic materials.

To fix the adapter 1.5 to the proximal component 1.1 and further to the distal component 1.2, the adapter 1.5 may be heated to enlarge the inner diameter and cooled down after connecting the proximal component 1.1 and the distal component 1.2 to generate a strong fit.

According to the embodiment illustrated in FIG. 6, the proximal component 1.1 and the distal component 1.2 respectively comprise a circumferential rim 1.1.2, 1.2.2 that are adapted to snap into corresponding notches arranged in the inner circumference of the adapter 1.5. For a robust snap connection, the adapter 1.5 needs to allow elastic deformation without cracking. This may be realized by selecting a plastic material as mentioned above.

According to the embodiment illustrated in FIG. 7, the adapter 1.5 and the distal component 1.2 are screwed together by a thread connection with threads being molded or formed onto the outer circumference of the distal component 1.2 and into the inner circumference of the adapter 1.5. This threaded connection may be combined with a bayonet lock. The proximal component 1.1 and the adapter 1.5 are connected to each other in a friction fit manner. That may be realized by a roughed or grinded surface R or grooves on an outer circumference of the proximal component 1.1.

The adapter 1.5 is required to ensure a fluid- and microbiologically tight connection between the components 1.1, 1.2. This may be achieved by including a gasket 1.5.2 (illustrated in FIG. 5B) to sealing surfaces of the adapter 1.5. The gasket 1.5.2 may be configured as an in-molded gasket that is formed by a two-component injection molding process. Alternatively, sealing rings (O-rings) can be arranged onto the sealing surfaces of the adapter 1.5. To tighten the connection between the components 1.1, 1.2, the components 1.1, 1.2 requires planar front faces. For plastic components, the molding processes can be designed to deliver planar parts; however, glass components may require a grinding process or may be manufactured applying laser-cutting processes that deliver the required surface quality.

An assembly of the two-chamber carpule 1 may be performed in four steps. A first step comprises the manufacturing of the proximal component 1.1 including the arrangement of the plug 1.3, filling, arrangement of a second plug (not illustrated), optional terminal sterilization and feed in to aseptic assembly zone. A second step may comprise arranging the adapter 1.5 on the proximal component 1.1. A third step may comprise attaching the distal component 1.2 to the adapter 1.5 and a fourth step may comprise aseptic filling and closure of the distal component 1.2.

Figure 8A:
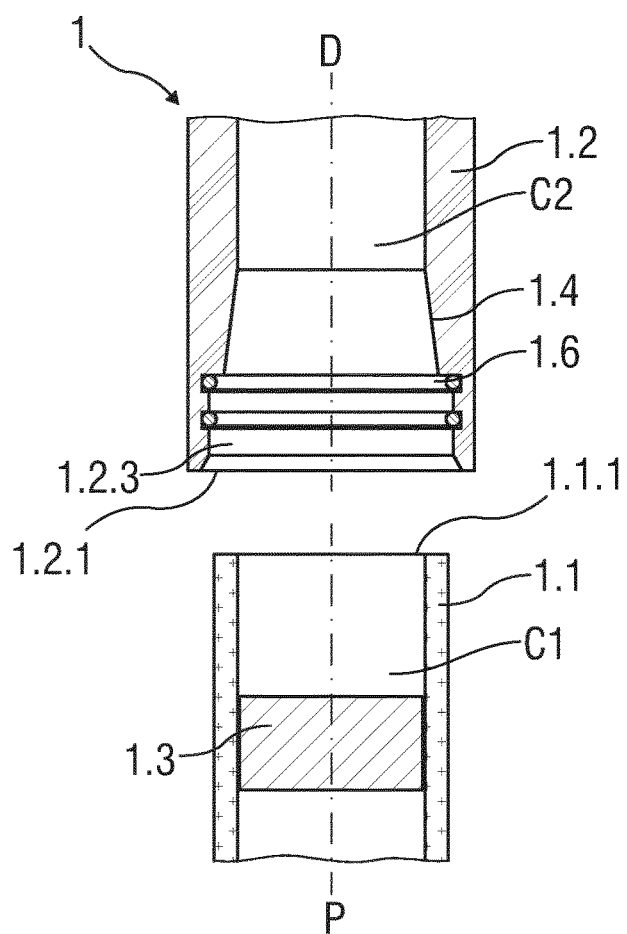
FIG. 8A is a schematic longitudinal section of an exemplary embodiment of an inventive two-chamber carpule comprising two components made from different materials before assembly.
Figure 8B:
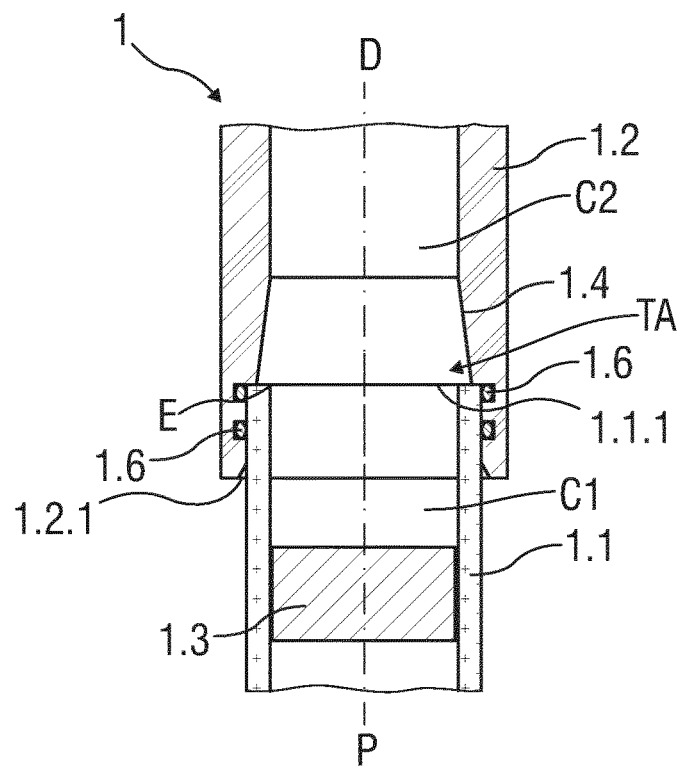
FIG. 8B is a schematic longitudinal section of the inventive two-chamber carpule according to FIG. 8A in an assembled state, wherein the components are plugged together.

The use of an adapter 1.5 allows connecting two components made of glass or a connection of glass to plastic in an easy manner. This allows reaching a high-speed assembly due to a linear movement of the connecting parts except a threaded connection as illustrated in FIG. 7. Here, linear and rotational movement of the components is required in combination with linear and angular position determination and torque force control. However, this manufacturing and assembly principles are well established. FIGS. 8A and 8B respectively show a schematic longitudinal section of an exemplary embodiment of a two-chamber carpule 1, wherein FIG. 8A illustrated the two-chamber carpule 1 before assembly and FIG. 8B illustrates the two-chamber carpule 1 in an assembled state.

The two-chamber carpule 1 is configured almost equally to the embodiment illustrated in FIGS. 2A and 2B. An inner diameter of the distal component 1.2 in the area of the dent 1.2.3 is dimensioned to allow the proximal component 1.1 to be pressed in the dent 1.2.3. Further, two sealing elements 1.6 will ensure tight connection between the components 1.1, 1.2. The sealing elements 1.6 are arranged within corresponding circumferential grooves in the inner circumference of the distal component 1.2 in the area of the dent 1.2.3 and being spaced from each other in an axial direction. One of the sealing elements 1.6 is arranged on a distal end of the dent 1.2.3. According to the present embodiment, the sealing elements 1.6 are configured respectively as a ring seal, i.e. an O-Ring.

Figure 9A:
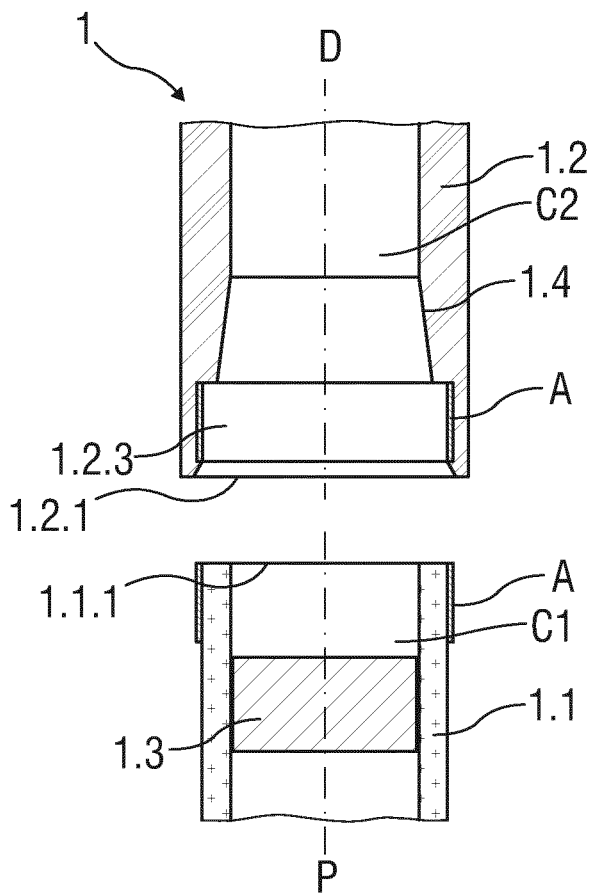
FIG. 9A is a schematic longitudinal section of an exemplary embodiment of an inventive two-chamber carpule comprising two components made from different materials and two sealing elements before assembly.
Figure 9B:
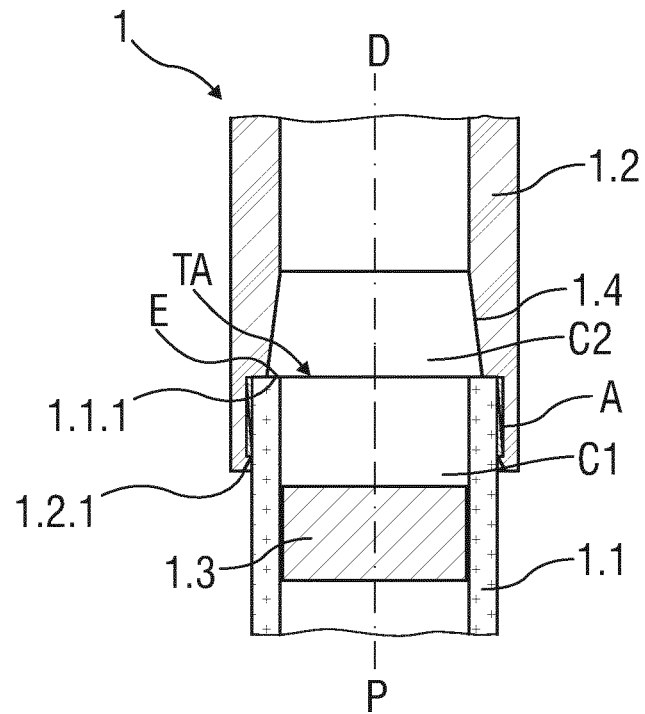
FIG. 9B is a schematic longitudinal section of the inventive two-chamber carpule according to FIG. 9A in an assembled state, wherein the components are glued together.

FIGS. 9A and 9B respectively show a schematic longitudinal section of an exemplary embodiment of a two-chamber carpule 1, wherein FIG. 9A illustrated the two-chamber carpule 1 before assembly and FIG. 9B illustrates the two-chamber carpule 1 in an assembled state.

The two-chamber carpule 1 is configured almost equally to the embodiment illustrated in FIGS. 2A and 2B. Connecting surfaces of the components 1.1, 1.2, in particular the inner circumference of the distal component 1.2 and the outer circumference of the proximal component 1.1 are provided with an adhesive A.

The application of the adhesive A, i.e. a light cure glue with fluorescent marker, on high speed assembly machines can be achieved by dosing nozzles that position droplets of the adhesive A on one or both of the surfaces on the inner circumference of the distal component 1.2 and the outer circumference of the proximal component 1.1, followed by assembling of the components 1.1, 1.2 and light-hardening of the adhesive A. To allow optimum strength of the bond, the circumferences provided with the adhesive A may have roughed or structured surfaces. A visual inspection of the adhesive distribution and quality of bonding may be followed by checking for fluorescence of the adhesive A on the circumferences.

An adhesive A may also be applied for creating a microbiologically tight and mechanically locked assembly of threaded components.

Figure 10A:
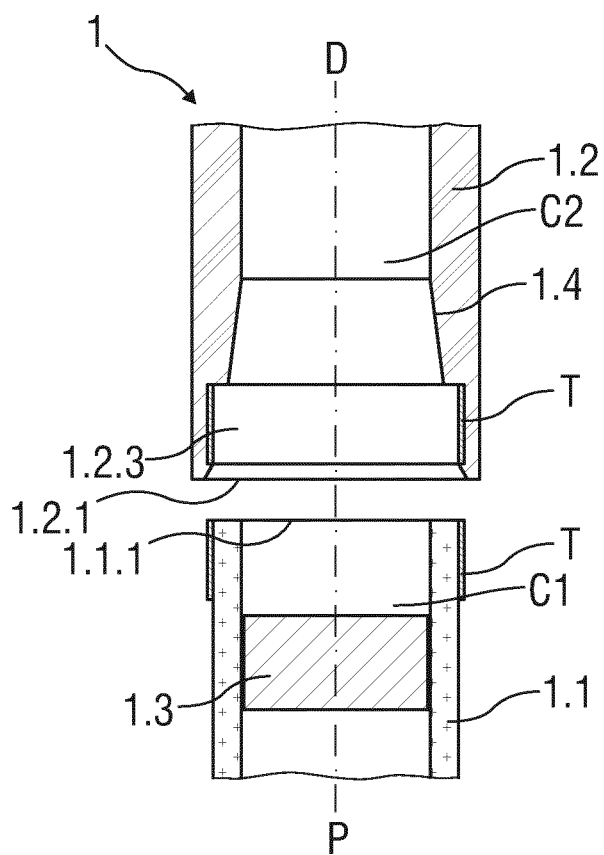
FIG. 10A is a schematic longitudinal section of an exemplary embodiment of an inventive two-chamber carpule comprising two components made from different materials and a molded component before assembly.
Figure 10B:
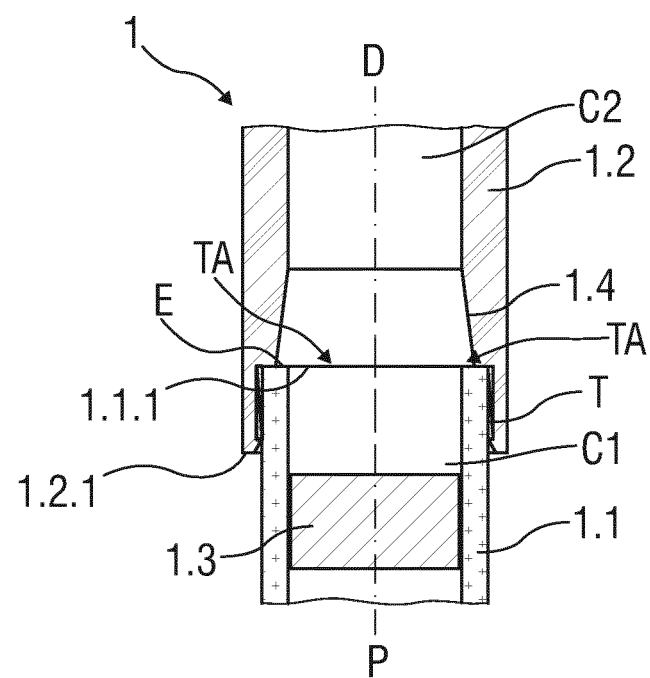
FIG. 10B is a schematic longitudinal section of the inventive two-chamber carpule according to FIG. 10A in an assembled state.

FIGS. 10A and 10B respectively show a schematic longitudinal section of an exemplary embodiment of a two-chamber carpule 1, wherein FIG. 10A illustrates the two-chamber carpule 1 before assembly and FIG. 10B illustrates the two-chamber carpule 1 in an assembled state.

The two-chamber carpule 1 is configured almost equally to the embodiment illustrated in FIGS. 9A and 9B except the adhesive A. Here, the interface areas of the components 1.1, 1.2 are provided with a molded component T, i.e. a layer of a thermoplastic elastomer (TPE).

The molded component T may be formed during manufacturing of the distal component 1.2 by applying a two-component injection molding process to reduce the number of parts to be handled in a production process. Alternatively, a separate ring-shaped layer of a thermoplastic elastomer may be attached to the interface area during the production process.

Material characteristics of the molded component T are selected in a way ensuring microbiologically tight sealing due to rubber-like properties at product handling and storage temperatures, e.g. temperatures from +2 degree to 30 degrees. A minimum thickness of the layer of thermoplastic elastomer reduces an impact of an elastic deformation and a mechanical strength of the bond increases with an increasing size of the interface area.

For assembly of the components 1.1, 1.2, the interface area of the distal component 1.2 may be heated up to soften the thermoplastic elastomer and to enlarge the inner diameter of the distal component 1.2. After insertion of the proximal component 1.1 into the distal component 1.2, the thermoplastic elastomer may be cooled down to an ambient temperature that leads to shrinking of the inner diameter of the distal component 1.2, thereby forming a strong mechanical bond. A roughed or microstructured surface of the interface area of the proximal component 1.1 further strengthens the mechanical bond between the components 1.1, 1.2.

Figure 11A:
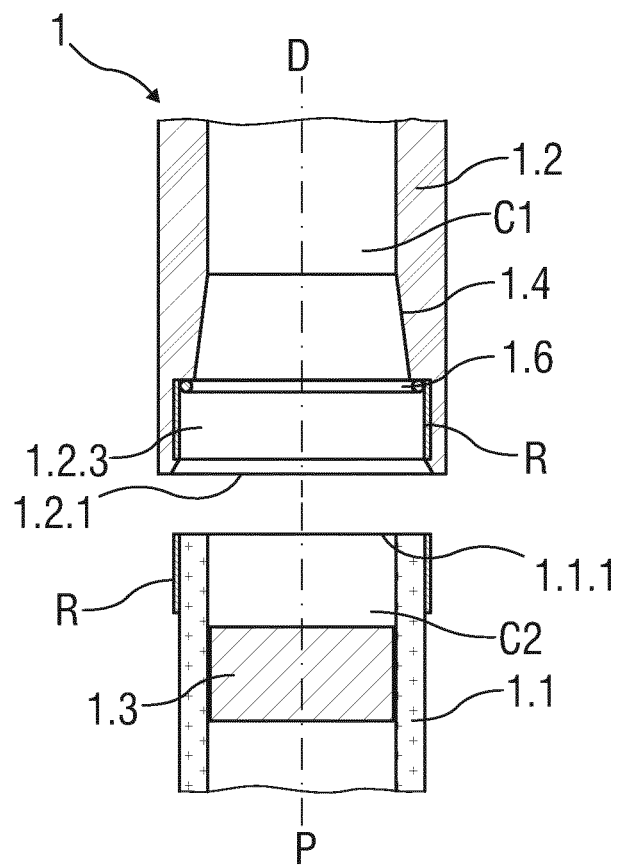
FIG. 11A is a schematic longitudinal section of an exemplary embodiment of an inventive two-chamber carpule comprising two components made from different materials, a sealing element and rough surfaces on the components before assembly.
Figure 11B:
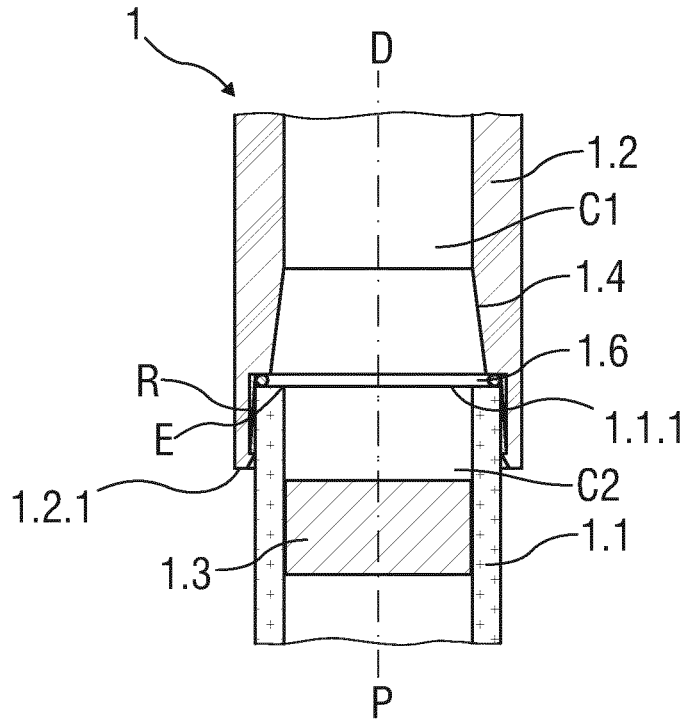
FIG. 11B is a schematic longitudinal section of the inventive two-chamber carpule according to FIG. 11A in an assembled state.

FIGS. 11A and 11B respectively show a schematic longitudinal section of an exemplary embodiment of a two-chamber carpule 1, wherein FIG. 11A illustrates the two-chamber carpule 1 before assembly and FIG. 11B illustrates the two-chamber carpule 1 in an assembled state.

The two-chamber carpule 1 is configured almost equally to the embodiments illustrated in FIGS. 10A to 10B. Instead of an adhesive A or a molded component T, the interface area is provided with roughed or grinded surfaces R on the outer circumference of the proximal component 1.1 and on the inner circumference of the distal component 1.2, in particular on the inner surface of the distal component 1.2 in the area of the dent 1.2.3.

The roughed surfaces lead to a friction between the components 1.1, 1.2 that ensures a tight connection by indentation of the roughed surfaces. A resulting friction force may be described by the following formula:

$$F_R = F_N \times \mu \qquad (1),$$

with: $F_R$: friction force
$F_N$ axial force
x raising parameter
$\mu$ friction coefficient.

Thus, the friction force is the result of multiplying the axial force with a friction coefficient $\mu$. The friction force can be further increased by the raising parameter, which may be defined by roughed or microstructured surfaces at the interface area. This frictional connection enables a mechanically stable connection between the components 1.1, 1.2.

To enable further a microbiologically tight connection, the two-chamber carpule 1 comprises one sealing element 1.6 that is arranged within a corresponding circumferential groove in the inner circumference of the distal component 1.2, in particular on a distal end of the dent 1.2.3, nearly similar to the embodiment illustrated in FIGS. 8A and 8B. According to the present embodiment, the sealing element 1.6 is configured as a ring seal, i.e. an O-ring. Alternatively, the sealing element 1.6 may be configured as a glue, a thermoplastic elastomer layer or ring or is formed by melting the plastic surface.

Figure 12A:
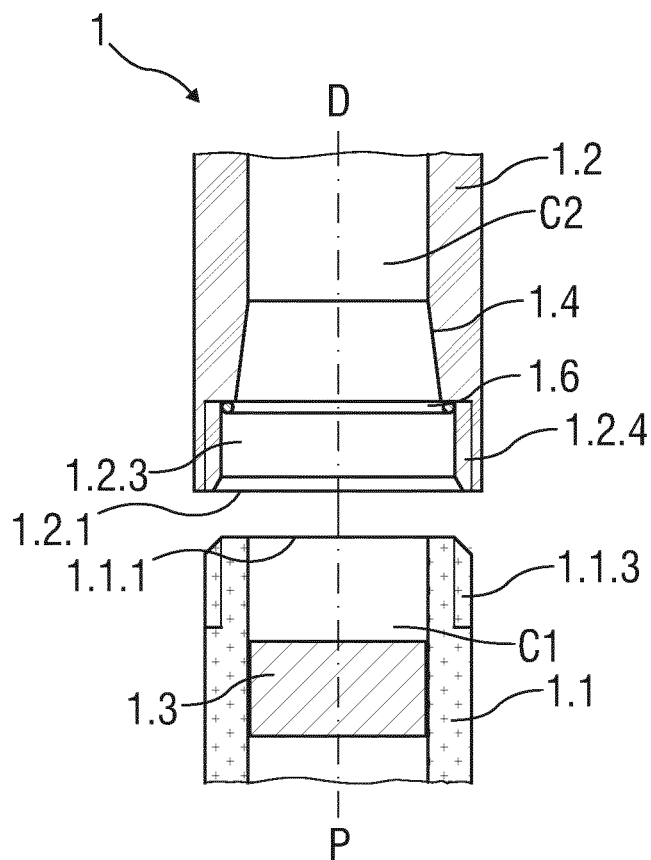
FIG. 12A is a schematic longitudinal section of an exemplary embodiment of an inventive two-chamber carpule comprising two components made from different materials, a sealing element and corresponding threads before assembly.
Figure 12B:
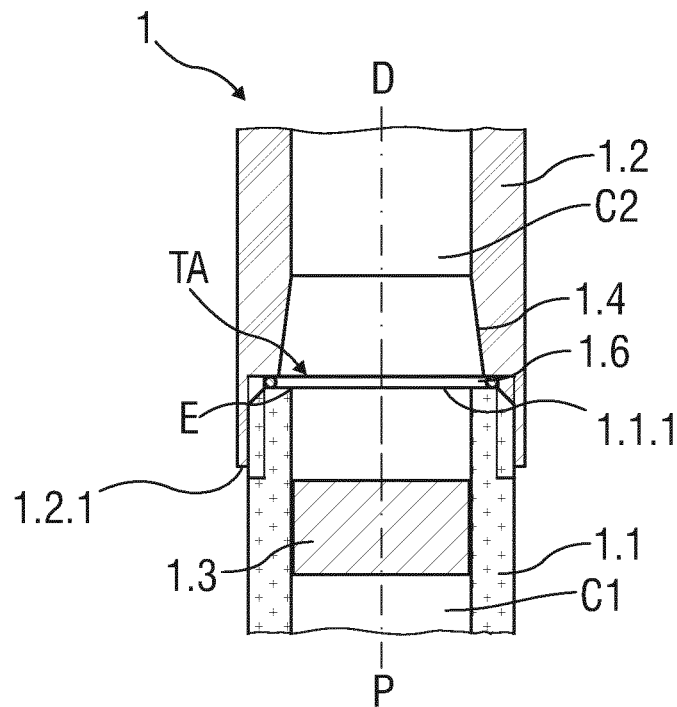
FIG. 12B is a schematic longitudinal section of the inventive two-chamber carpule according to FIG. 12A in an assembled state, wherein the components are screwed together.

FIGS. 12A and 12B respectively show a schematic longitudinal section of an exemplary embodiment of a two-chamber carpule 1, wherein FIG. 12A illustrates the two-chamber carpule 1 before assembly and FIG. 12B illustrates the two-chamber carpule 1 in an assembled state.

The components 1.1, 1.2 are joined together by a screw thread similar to the conventional embodiment illustrated in FIG. 1. The proximal component 1.1 comprises the outer thread 1.1.3 and the distal component 1.2 comprises the corresponding inner thread 1.2.4. The inner diameter of the distal component 1.2 is larger than the outer diameter of the proximal component 1.1 due to the dent 1.2.3. The bevel 1.4 is located axially behind the dent 1.2.3 in a direction away from the proximal component 1.1 as before. Screwing the distal component 1.2 on the proximal component 1.1 in combination with an elasticity of the plastic material of the inner thread 1.2.4 and the sealing element 1.6 will ensure a tight connection between the components 1.1, 1.2.

Figure 13A:
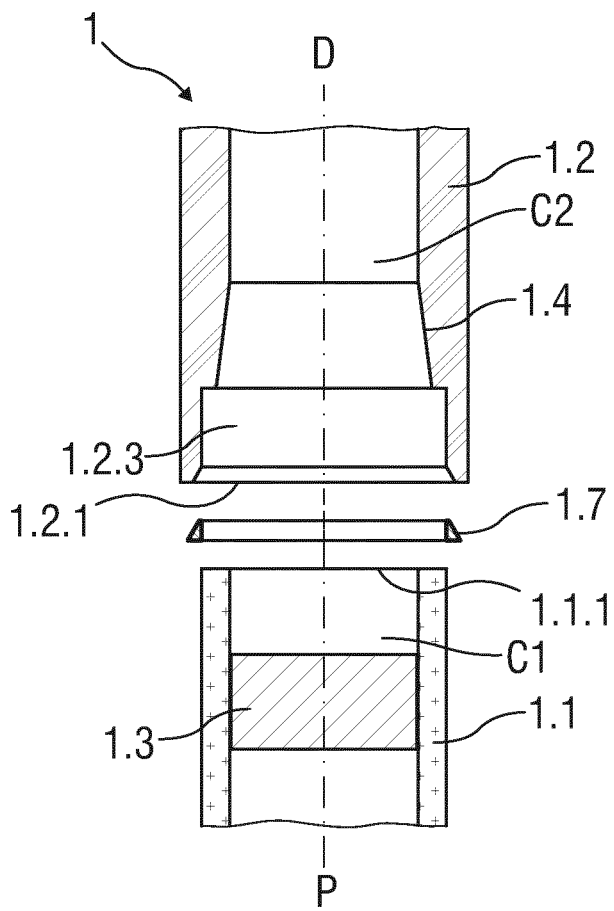
FIG. 13A is a schematic longitudinal section of an exemplary embodiment of an inventive two-chamber carpule comprising two components made from different materials and a clamp element before assembly.
Figure 13B:
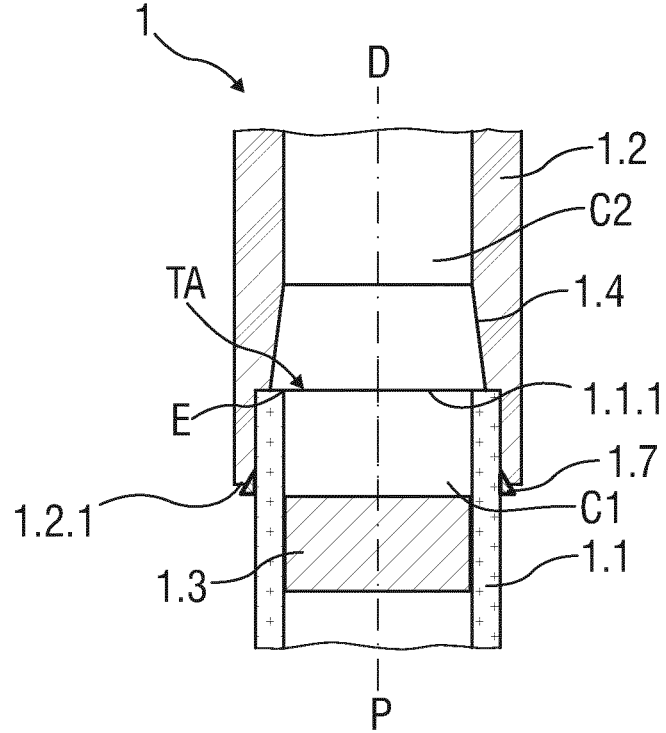
FIG. 13B is a schematic longitudinal section of the inventive two-chamber carpule according to FIG. 13A in an assembled state.

FIGS. 13A and 13B respectively show a schematic longitudinal section of an exemplary embodiment of a two-chamber carpule 1, wherein FIG. 13A illustrates the two-chamber carpule 1 before assembly and FIG. 13B illustrates the two-chamber carpule 1 in an assembled state.

The two-chamber carpule 1 is configured almost equally to the general embodiment illustrated in FIGS. 2A and 2B. In addition to, the two-chamber carpule 1 comprises a clamp element 1.7 that is arranged between the proximal component 1.1 and the distal component 1.2 in the area of a proximal end 1.2.1 of the distal component 1.2.

According to the present embodiment, the clamp element 1.7 is configured as a clamp ring comprising an outer diameter that dilates conically. The clamp element 1.7 leads to a friction between the components 1.1, 1.2 that ensures a tight connection. A resulting friction force may be described by the formula (1). The two-chamber carpule 1 may also comprise a sealing element as illustrated in FIGS. 12A and 12B.

Figure 14A:
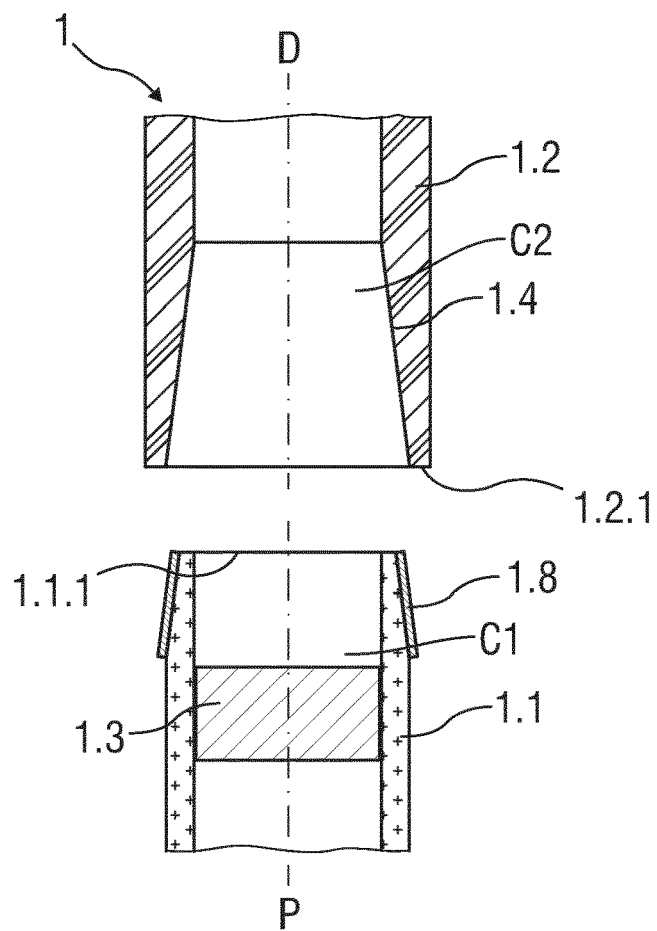
FIG. 14A is a schematic longitudinal section of an exemplary embodiment of an inventive two-chamber carpule comprising two components made from different materials before assembly, wherein one of the components comprises an enlarged surface.
Figure 14B:
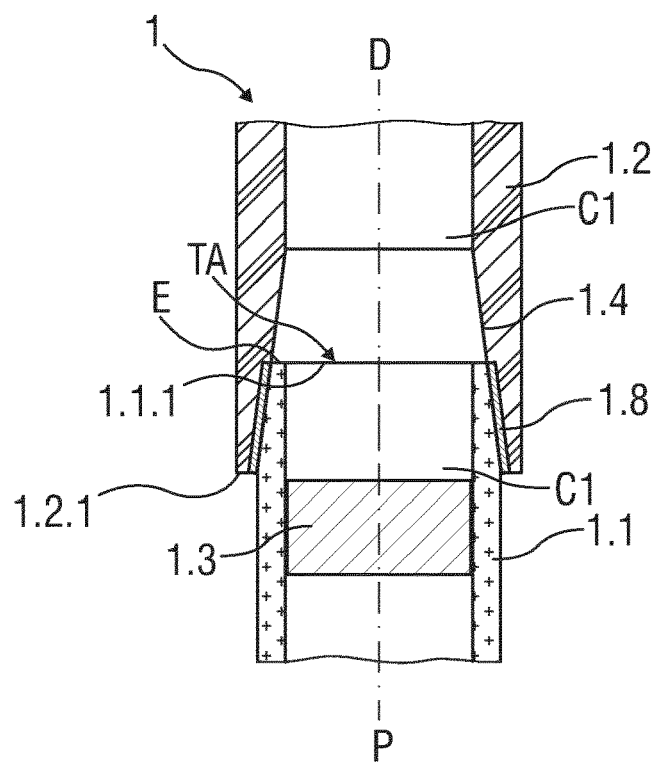
FIG. 14B is a schematic longitudinal section of the inventive two-chamber carpule according to FIG. 14A in an assembled state, wherein the components are glued together.

FIGS. 14A and 14B respectively show a schematic longitudinal section of an exemplary embodiment of a two-chamber carpule 1, wherein FIG. 14A illustrates the two-chamber carpule 1 before assembly and FIG. 14B illustrates the two-chamber carpule 1 in an assembled state.

According to the present embodiment, the bevel 1.4 in the distal component 1.2 corresponds to a further bevel 1.8 on an outer circumference of the proximal component 1.1. Thus, a section of the outer circumference of the proximal component 1.1 and a section of the inner circumference of the distal component 1.2 are formed as truncated cones with a rough surface area. Due to the corresponding beveled circumferences, a friction area is enlarged compared to not-beveled circumferences, thereby enabling a tight connection. A combination with glue or a layer of thermoplastic elastomer may be done.

Figure 15A:
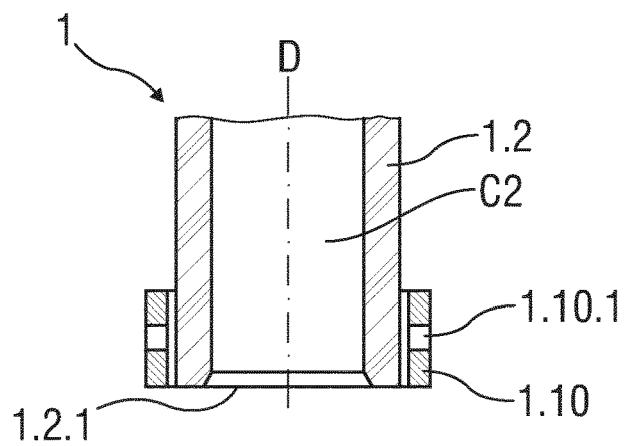
FIG. 15A is a schematic longitudinal section of an exemplary embodiment of an inventive two-chamber carpule comprising two components made from different materials and bayonet elements before assembly.
Figure 15A:
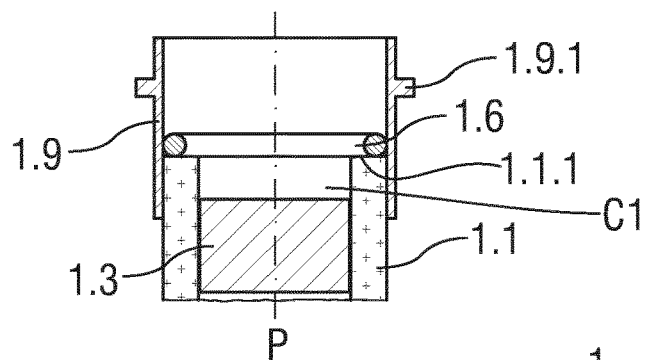
Figure 15B:
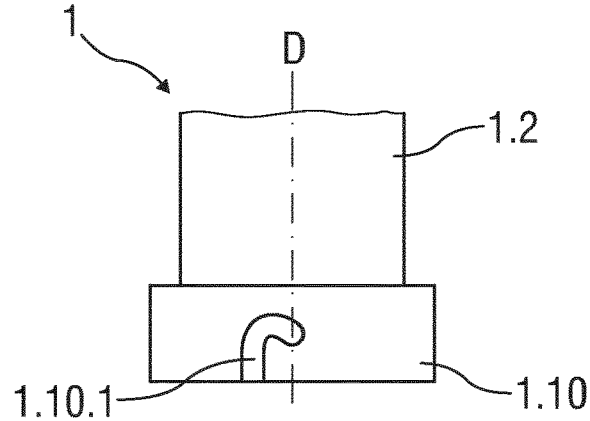
FIG. 15B is a schematic side view of the inventive two-chamber carpule according to FIG. 13B before assembly.
Figure 15B:
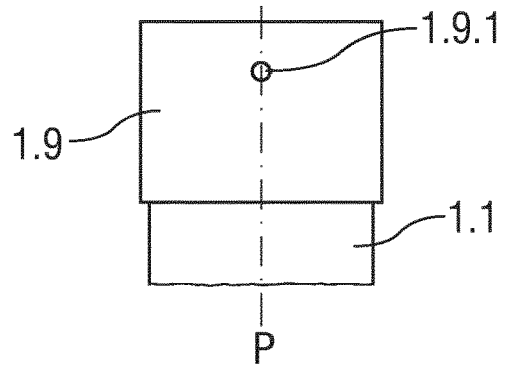
Figure 15C:
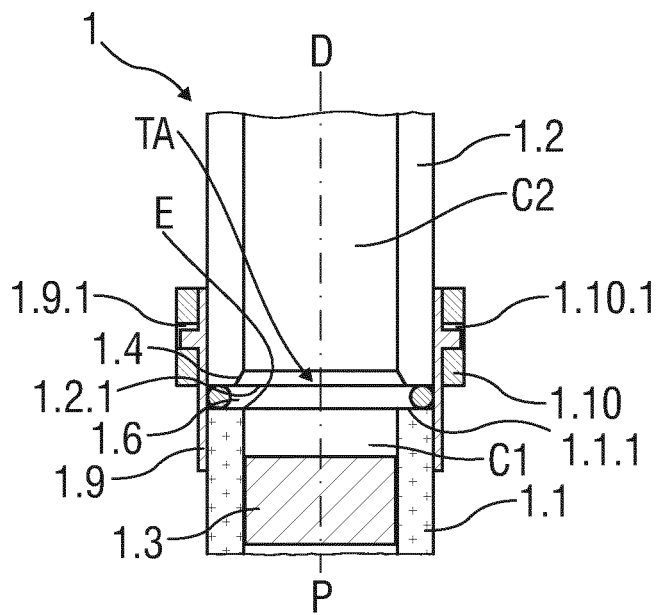
FIG. 15C is a schematic longitudinal section of the inventive two-chamber carpule according to FIGS. 15A and 15B in an assembled state.

FIGS. 15A to 15C respectively show an exemplary embodiment of a two-chamber carpule 1, wherein FIG. 15A illustrates a longitudinal view of the two-chamber carpule 1 before assembly, FIG. 15B illustrates a side view of the two-chamber carpule 1 before assembly and FIG. 15C illustrates a longitudinal section of the two-chamber carpule 1 in an assembled state.

According to the present embodiment, the components 1.1, 1.2 are joined together via a bayonet fitting. For this, the proximal component 1.1 is provided with a male attachment 1.9, which is configured as a hollow cylinder surrounding a front end of the proximal component 1.1 facing the distal component 1.2, thereby protruding axially from the front end of the proximal component 1.1. The male attachment 1.9 comprises two protrusions 1.9.1 arranged on an outer circumference and protruding radially outwards from the outer circumference. The distal component 1.2 is provided with a female attachment 1.10, which is configured as a hollow cylinder surrounding the proximal end 1.2.1 of the distal component 1.2. The female attachment 1.10 is radially spaced from the outer circumference of the distal component 1.2 at least section-wise in order to receive the male attachment 1.9 during assembly. The female attachment 1.10 comprises two slots 1.10.1 adapted to receive the protrusions 1.9.1 to create the bayonet fitting. By axially aligning the orientation of the protrusions 1.9.1 and the slots 1.10.1 and pushing the male attachment 1.9 into the female attachment 1.10, followed by rotating the components 1.1, 1.2 against each other, the connection between the components 1.1, 1.2 is ensured.

Additionally, the two-chamber carpule 1 is provided with a sealing element 1.6, which may be configured of an elastic plastic material, e. g. synthetic rubber, and that may be adapted to form a gasket between the components 1.1, 1.2. Due to a compression of the elastic sealing element 1.6 during assembly, a reset force is applied ensuring that the connection of the components 1.1, 1.2 will be maintained.

Furthermore, the bevel 1.4 has smaller dimensions compared with the embodiments illustrated in FIGS. 2A to 15B. Nonetheless, the bevel 1.4 provides that no protruding edge is formed by assembly of the components 1.1, 1.2 that might impair the movement of the plug 1.3 across the transition area TA of the components 1.1, 1.2.

Figure 16A:
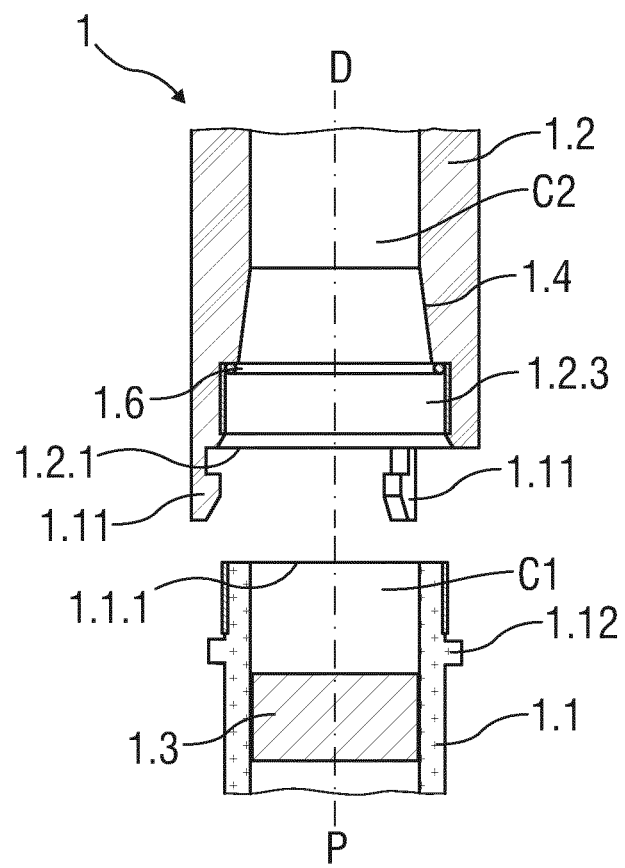
FIG. 16A is a schematic longitudinal section of an exemplary embodiment of an inventive two-chamber carpule comprising two components made from different materials and snap elements before assembly.
Figure 16B:
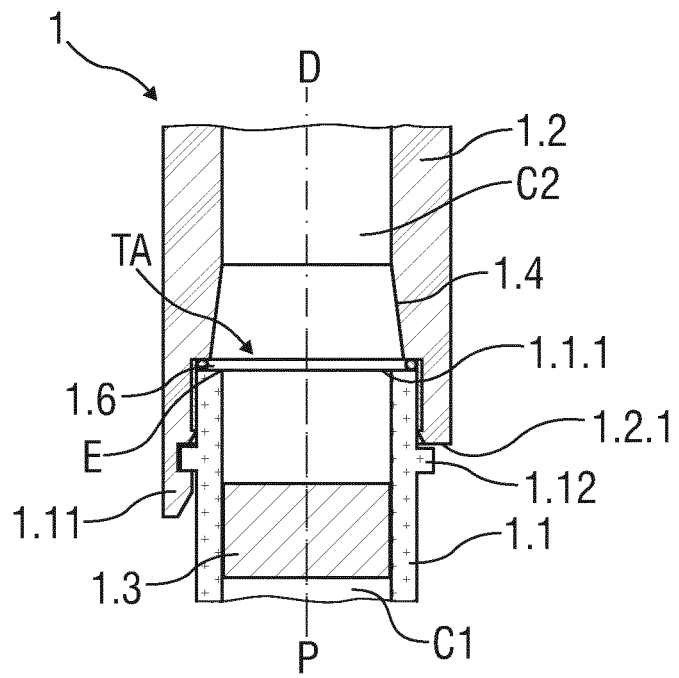
FIG. 16B is a schematic longitudinal section of the inventive two-chamber carpule according to FIG. 16A in an assembled state.
Figure 16C:
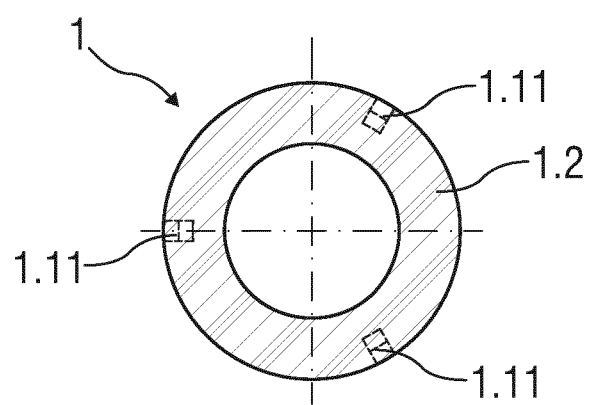
FIG. 16C is a schematic cross section of the inventive two-chamber carpule according to FIG. 16B.

FIGS. 16A to 16C respectively show an exemplary embodiment of a two-chamber carpule 1, wherein FIG. 16A illustrates a longitudinal view of the two-chamber carpule 1 before assembly, FIG. 16B illustrates a cross section of the two-chamber carpule 1 in an assembled state and FIG. 16C illustrates a longitudinal section of the two-chamber carpule 1 in the assembled state.

According to the present embodiment, the components 1.1, 1.2 are joined together via a snap fitting. For this, the distal component 1.2 comprises locking arms 1.11 with hooks on a free end respectively. The locking arms 1.11 protrude axially from the proximal end 1.2.1 of the distal component 1.2. For example, there are arranged three locking arms 1.11 distributed around the circumference of the distal component 1.2. Alternatively, there may be arranged less or more than three locking arms 1.11. The proximal component 1.1 comprises corresponding locking projections 1.12 that may be configured as separate projections distributed around the outer circumference of the proximal component 1.1 or as a circumferential ring.

Furthermore, the two-chamber carpule 1 is provided with a sealing element 1.6, which may be configured similar to the sealing element 1.6 in the embodiment illustrated and described in FIGS. 12A and 12B.

In contrast to the present embodiment, the components 1.1, 1.2 may be both made from a plastic material in order to enable an easy manufacturing of the locking projections 1.12.

The snap fit provides a safety mechanism against loosening of a friction fit or an adhesive connection and maintaining pressure on the sealing element 1.6 between the components 1.1, 1.2.

FIGS. 17A and 17B respectively show a schematic longitudinal section of an exemplary embodiment of a two-chamber carpule 1, wherein FIG. 17A illustrates the two-chamber carpule 1 before assembly and FIG. 17B illustrates the two-chamber carpule 1 in an assembled state.

According to the present embodiment, the components 1.1, 1.2 are melted together. The outer diameter of the proximal component 1.1 is slightly larger than the inner diameter of the dent 1.2.3 in the distal component 1.2. If heat is applied to the interface area of the distal component 1.2, the diameter of the dent 1.2.3 will be increased, thereby allowing assembly of the components 1.1, 1.2. A subsequent cooling down of the heated area to an ambient temperature causes a shrinking of the diameter of the dent 1.2.3. This leads to a strong mechanical bond.

Furthermore, the outer circumference of the proximal component 1.1 may comprise a roughed surface in the transition area TA. An inserted sealing element 1.6 between the components 1.1, 1.2 as illustrated in the present embodiment ensures a microbiologically tight connection.

Figure 18A:
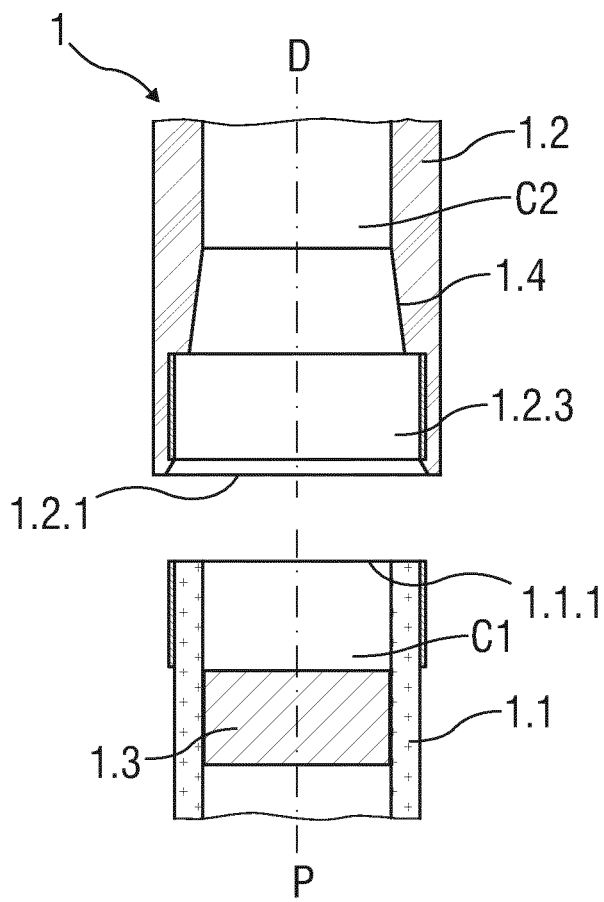
FIG. 18A is a schematic longitudinal section of an exemplary embodiment of an inventive two-chamber carpule comprising two components made from different materials before assembly.
Figure 18B:
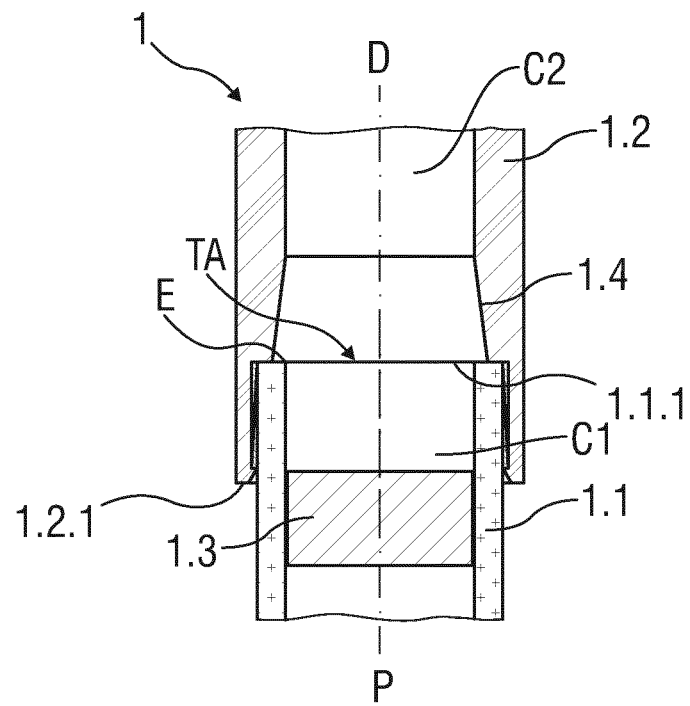
FIG. 18B is a schematic longitudinal section of the inventive two-chamber carpule according to FIG. 18A in an assembled state, wherein the components are welded together

FIGS. 18A and 18B respectively show a schematic longitudinal section of an exemplary embodiment of a two-chamber carpule 1, wherein FIG. 18A illustrates the two-chamber carpule 1 before assembly and FIG. 18B illustrates the two-chamber carpule 1 in an assembled state.

According to the present embodiment, the components 1.1, 1.2 are joined together by laser welding in the interface area.

A contact-free laser welding device enables a tensionless component, which avoids the emergence of micro cracks. This leads to a reduction of process steps, saving costs and work space. Furthermore, this leads to a higher yield for mass production and consequently low cost of ownership. Laser welding of glass materials requires low thermal conductivity of the material, which creates high temperature gradients when heated up locally and hence, may involve a breakage.

After pre-heating the glass material, the laser process can be optimized in order to control the risk of breakage. Using a defocused laser beam reduces the temperature gradient within the welding zone compared to other joining techniques and it benefits essentially from the sterile surface quality. Besides metals, a wide variety of other materials can be laser processed: i.e semiconductors, plastics, organic materials, ceramics, paper, glass, graphite, diamonds and also composite materials.

Figure 19:
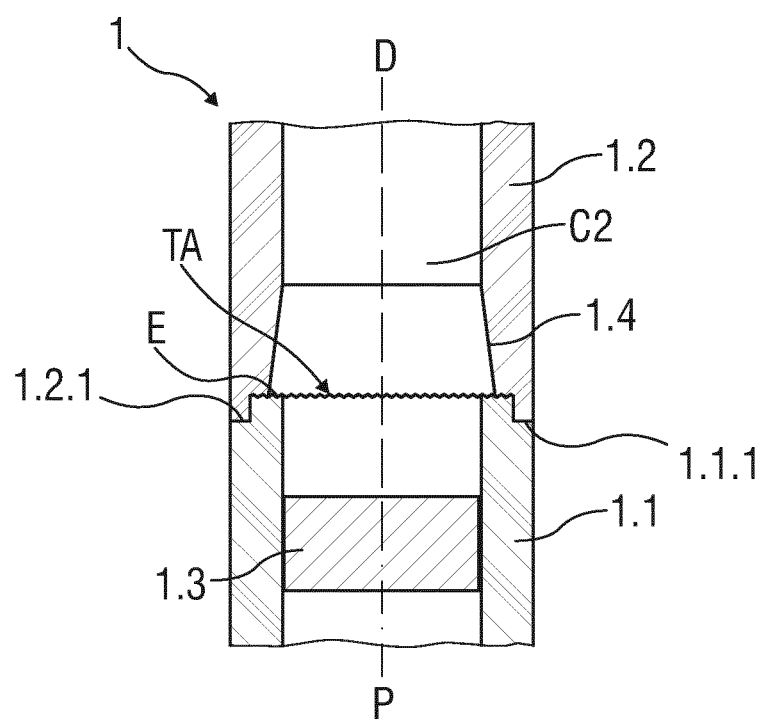
FIG. 19 is schematic longitudinal section of an exemplary embodiment of an inventive two-chamber carpule comprising two components made from the same material in an assembled state, wherein the components are welded together.

FIG. 19 shows a schematic longitudinal section of an exemplary embodiment of a two-chamber carpule 1 in an assembled state comprising two components 1.1, 1.2 made from a plastic material.

Here, the distal component 1.2 and the proximal component 1.1 are welded together to achieve both, a strong bond and a microbiologically tight connection. Welding processes may be performed as infrared, ultrasonic, laser or induction welding.

Ultrasonic welding may be performed very fast. Assembly rates of more than 25 parts per minute are possible with a single station. There are no secondary operations, such as coating, inserting, or cleaning. The welding process requires fairly rigid materials. Dissimilar-material-sonic-welds are possible, but melting temperatures of both materials have to be quite close, otherwise, only the lower-melting material will soften and a bond will not form.

Induction welding is a high-cost technique and is suitable for difficult-to-weld plastics such as polypropylene, and for shapes that cannot be fitted into an ultrasonic welding machine. The process is best suited for bonding most polypropylene, polyethylene, styrene, ABS, polyester and nylon in high-volume, highly automated joining operations. Heat-resistant polypropylenes that cannot be joined with adhesives or other welding techniques may be successfully joined using induction welding. Bonding agents heated inductively reach temperatures of 300 degrees Fahrenheit in 0.1 second to fuse with the heat-resistant substances. Alternatively, the components 1.1, 1.2 may be fused by fusion bonding or solvent bonding.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −2° C. to about 4° C. to 8° C.). In some instances, the drug container may be or may include a dual-chamber cartridge configured to store two or more components of a drug formulation (e.g., a drug and a diluent, or two different types of drugs) separately, one in each chamber. In such instances, the two-chambers of the dual-chamber cartridge may be configured to allow mixing between the two or more components of the drug or medicament prior to and/or during dispensing into the human or animal body. For example, the two-chambers may be configured such that they are in fluid communication with each other (e.g., by way of a conduit between the two-chambers) and allow mixing of the two components when desired by a user prior to dispensing. Alternatively or in addition, the two-chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')$_2$ fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient.

Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof

LIST OF REFERENCES

1' two-chamber carpule
1.1' component, proximal component
1.1.1' distal end
1.1.2' proximal end
1.1.3' extension
1.2' component, distal component
1.2.1' proximal end
1.2.2' distal end
1.2.3' indentation
1.3.1', 1.3.2' plug
1.5' membrane
1.6' sealing element
1.7' bypass
1.8' cap
1.8.1' sealing disc
1.8.2' fixing sleeve
C1', C2' chamber
1 two-chamber carpule
1.1 component, proximal component
1.1.1 distal end
1.1.2 circumferential rim
1.1.3 outer thread
1.2 component, distal component
1.2.1 proximal end
1.2.2 circumferential rim
1.2.3 dent
1.2.4 inner thread
1.3 plug
1.4 bevel
1.5 adapter
1.5.1 stop
1.5.2 gasket
1.6 sealing element
1.7 clamp element
1.8 further bevel
1.9 male attachment
1.9.1 protrusion
1.10 female attachment
1.10.1 slot
1.11 locking arm
1.12 locking projection
A adhesive
C1, C2 chamber
D distal direction
E edge
P proximal direction
T molded component
TA transition area
R roughed or grinded surface

The invention claimed is:

1. A two-chamber carpule comprising:
a first chamber and a second chamber adapted to be joined together, each chamber adapted to contain a medicament component, the first and second chambers formed by respective separate first and second components, the separate first and second components being axially joined together, and
a bevel arranged on an inner circumference of at least one of the first and second components in a transition area, extending from the first component to the second component, wherein the transition area provides an edge to block a movement of a plug in a determined direction.

2. The two-chamber carpule according to claim 1, wherein the edge is formed by a distal end of the first component that comprises an inner diameter less than an inner diameter of the second component in the transition area, due to the bevel.

3. The two-chamber carpule according to claim 2, wherein at least one section of an inner circumference of the second component is bevelled such that the inner diameter of the second component decreases in a direction away from the first component.

4. The two-chamber carpule according to claim 3, wherein the inner diameter of the first component is less than or equal to the inner diameter of the second component having the bevel.

5. The two-chamber carpule according to claim 1, wherein at least one section of an inner circumference of the first component is bevelled such that an inner diameter of the first component decreases in a direction facing the second component.

6. The two-chamber carpule according to claim 1, wherein the second component is made from a plastic material and the first component is made from a glass material.

7. The two-chamber carpule according to claim 1, wherein the first and second components are made from a glass material or from a plastic material.

8. The two-chamber carpule according to claim 1, wherein the first and second components are axially joined together by a bayonet fitting comprising at least one protrusion and a corresponding slot.

9. The two-chamber carpule according to claim 1, wherein the first and second components are axially joined together by a snap fitting comprising at least one locking arm and a corresponding locking projection.

10. The two-chamber carpule according to claim 1, wherein the first and second components are axially plugged together.

11. The two-chamber carpule according to claim 10, wherein the first and second components respectively comprise a rough surface in an interface area of the plugged first and second components.

12. The two-chamber carpule according to claim 10, wherein a clamp element is arranged between the plugged first and second components.

13. The two-chamber carpule according to claim 1, wherein a sealing element is arranged between the axially joined components.

14. A method of assembly of the two-chamber carpule according to claim 1, the method comprising:
joining the first chamber and the second chamber in a force fitting, form fitting, or firmly bonding manner.

15. The method according to claim 14, comprising:
manufacturing the first component and the second component, wherein the first component forms the first chamber and the second component forms the second chamber,
filling the first component with a medicament component and closing the first component,
axially joining the first and second components, and
filling the second component with a medicament component and closing the second component.

16. The method according to claim 15, wherein closing the first component comprises:
inserting at least one plug into the chamber.

17. The method according to claim 15, wherein axially joining the first and second components comprises force fitting the first and second components.

18. The method according to claim 15, wherein axially joining the first and second components comprises form fitting the first and second components.

19. The method according to claim 15, wherein axially joining the first and second components comprises firmly bonding the first and second components.

20. A two-chamber carpule comprising:
a first chamber and a second chamber adapted to be joined together, each chamber adapted to contain a medicament component, the first and second chambers formed by respective separate first and second components, the separate first and second components being axially joined together, and
a bevel arranged on an inner circumference of at least one of the first and second components in a transition area, extending from the first component to the second component, wherein the transition area provides an edge to block a movement of a plug in a determined direction,
wherein a length of the bevel is larger than a distance between the edge and the bevel.

* * * * *